(12) United States Patent
Dow et al.

(10) Patent No.: US 10,111,761 B2
(45) Date of Patent: Oct. 30, 2018

(54) METHOD OF CONTROLLING PROSTHETIC DEVICES WITH SMART WEARABLE TECHNOLOGY

(71) Applicant: International Business Machines Corporation, Armonk, NY (US)

(72) Inventors: Eli M. Dow, Wappingers Falls, NY (US); Thomas D. Fitzsimmons, Poughkeepsie, NY (US); Joseph D. Harvey, Binghamton, NY (US); Douglas E. Rohde, East Meadow, NY (US)

(73) Assignee: International Business Machines Corporation, Armonk, NY (US)

( * ) Notice: Subject to any disclaimer, the term of this patent is extended or adjusted under 35 U.S.C. 154(b) by 354 days.

(21) Appl. No.: 14/862,190

(22) Filed: Sep. 23, 2015

(65) Prior Publication Data

US 2016/0378100 A1    Dec. 29, 2016

Related U.S. Application Data

(63) Continuation of application No. 14/753,323, filed on Jun. 29, 2015.

(51) Int. Cl.
*G05B 15/02* (2006.01)
*A61F 2/70* (2006.01)
(Continued)

(52) U.S. Cl.
CPC ............ *A61F 2/70* (2013.01); *G05B 15/02* (2013.01); *G05B 19/4155* (2013.01); *G06F 1/163* (2013.01); *G05B 2219/45168* (2013.01)

(58) Field of Classification Search
CPC ....... A61F 2/70; G05B 19/4155; G05B 15/02; G05B 2219/45168; G06F 1/163
See application file for complete search history.

(56) References Cited

U.S. PATENT DOCUMENTS

| 8,562,558 B2 * | 10/2013 | Kamath | ............... A61B 5/0002 604/66 |
| 8,686,947 B2 * | 4/2014 | Wine | ...................... G06F 1/163 345/169 |

(Continued)

FOREIGN PATENT DOCUMENTS

WO    2013038187 A1    3/2013

OTHER PUBLICATIONS

Chen, C.-H.; Naidu, D.S.; Perez-Gracia, A. and Schoen, M.P., "Hybrid Control Strategy for Five-Fingered Smart Prosthetic Hand", Dec. 16-18, 2009, Joint 48th IEEE Converence on Decision and Control and 28th Chinese Control Conference.*

(Continued)

*Primary Examiner* — Mohammad Ali
*Assistant Examiner* — Kelvin Booker
(74) *Attorney, Agent, or Firm* — Isaac J. Gooshaw

(57) ABSTRACT

A method, computer program product and computer system for mode selection of a prosthesis is provided. A processor of a wearable device receives a first input from a user. A processor of a wearable device determines the first input indicates a change to a mode of operation of the prosthesis. A processor of a wearable device sends a first command to the prosthesis to change the mode of operation of the prosthesis.

5 Claims, 3 Drawing Sheets

(51) Int. Cl.
*G06F 1/16* (2006.01)
*G05B 19/4155* (2006.01)

(56) References Cited

U.S. PATENT DOCUMENTS

| | | | | |
|---|---|---|---|---|
| 8,881,774 B2* | 11/2014 | Lanier, Jr. | ............. | A61J 1/2065 141/21 |
| 8,900,188 B2* | 12/2014 | Blumberg, Jr. | ...... | A61M 5/1413 604/151 |
| 9,582,076 B2* | 2/2017 | Kienzle | ................... | G06F 3/014 |
| 9,618,907 B2* | 4/2017 | Su | ........................... | G04G 17/02 |
| 9,648,926 B2* | 5/2017 | Marks | .................... | A43D 1/025 |
| 9,651,992 B2* | 5/2017 | Stotler | .................... | G06F 1/163 |
| 9,696,822 B2* | 7/2017 | Dow | ...................... | G06F 3/0362 |
| 9,733,700 B2* | 8/2017 | Song | ....................... | G06F 3/011 |
| 9,836,142 B2* | 12/2017 | Craig | .................... | G06F 3/0362 |
| 9,880,620 B2* | 1/2018 | Kienzle | .................. | G06F 3/014 |
| 2002/0163495 A1* | 11/2002 | Doynov | ................. | G06F 3/014 345/156 |
| 2003/0120183 A1* | 6/2003 | Simmons | .................. | A61F 4/00 600/595 |
| 2005/0052412 A1* | 3/2005 | McRae | .................... | A63F 13/06 345/158 |
| 2005/0240879 A1* | 10/2005 | Law | ........................ | G06F 1/1613 715/773 |
| 2006/0167564 A1* | 7/2006 | Flaherty | ............... | A61B 5/0476 623/57 |
| 2006/0195197 A1* | 8/2006 | Clausen | ............... | A61B 5/1038 623/24 |
| 2008/0191864 A1* | 8/2008 | Wolfson | ................... | G06F 3/011 340/524 |
| 2010/0072565 A1* | 3/2010 | Liu | .................... | B01L 3/502707 257/417 |
| 2010/0268351 A1 | 10/2010 | van der Merwe et al. | | |
| 2011/0046748 A1* | 2/2011 | Martin | ...................... | A61F 2/68 623/34 |
| 2011/0060421 A1* | 3/2011 | Martin | ...................... | A61F 2/68 623/34 |
| 2011/0210931 A1* | 9/2011 | Shai | ........................ | G06F 3/014 345/173 |
| 2011/0264238 A1* | 10/2011 | van der Merwe | ........ | A61F 2/54 623/24 |
| 2012/0075173 A1* | 3/2012 | Ashbrook | ............... | G06F 3/014 345/156 |
| 2013/0282117 A1* | 10/2013 | Van Heugten | ........ | A61F 2/1624 623/6.22 |
| 2014/0139454 A1* | 5/2014 | Mistry | .................... | G06F 3/041 345/173 |
| 2014/0143737 A1* | 5/2014 | Mistry | ................... | G06F 3/0488 715/854 |
| 2014/0143784 A1* | 5/2014 | Mistry | ................ | G06F 15/0208 718/102 |
| 2014/0143785 A1* | 5/2014 | Mistry | .................... | G06F 1/163 718/104 |
| 2014/0230563 A1* | 8/2014 | Huang | .................. | A61B 5/1038 73/841 |
| 2014/0268607 A1* | 9/2014 | Wicker | ................ | H05K 1/0284 361/761 |
| 2014/0354402 A1* | 12/2014 | Joao | .................... | G07C 9/00571 340/5.52 |
| 2015/0054630 A1* | 2/2015 | Xu | ........................... | G06F 3/017 340/12.5 |
| 2015/0230734 A1* | 8/2015 | Cheung | ................ | A61B 5/1123 702/141 |
| 2015/0262497 A1* | 9/2015 | Landau | .............. | G09B 19/0038 434/247 |
| 2015/0268721 A1* | 9/2015 | Joo | .................... | G02B 27/0093 345/156 |
| 2015/0298654 A1* | 10/2015 | Joao | ........................ | G01S 19/13 701/2 |
| 2015/0366504 A1* | 12/2015 | Connor | .................. | A61B 5/6804 600/301 |
| 2015/0370320 A1* | 12/2015 | Connor | ................ | A61B 5/6831 345/173 |
| 2015/0373443 A1* | 12/2015 | Carroll | .................. | H04B 1/385 381/364 |
| 2016/0018790 A1* | 1/2016 | Su | .......................... | G04G 17/02 368/316 |
| 2016/0019423 A1* | 1/2016 | Ortiz | ................... | G06K 9/00885 345/633 |
| 2016/0041804 A1* | 2/2016 | Wan | ........................ | G06F 1/163 345/1.3 |
| 2016/0131677 A1* | 5/2016 | Bostick | .............. | G06K 9/00335 73/865.4 |
| 2016/0195928 A1* | 7/2016 | Wagner | ................... | G06F 3/016 345/156 |
| 2016/0196758 A1* | 7/2016 | Causevic | ................. | G09B 5/00 434/236 |
| 2016/0367202 A1* | 12/2016 | Carter | ...................... | A61B 5/02 |
| 2016/0378100 A1* | 12/2016 | Dow | ......................... | A61F 2/70 700/275 |
| 2016/0378184 A1* | 12/2016 | Dow | ..................... | G06F 3/0227 345/173 |
| 2017/0031491 A1* | 2/2017 | Bao | ........................ | G06F 3/0414 |
| 2017/0078850 A1* | 3/2017 | Bostick | ................. | H04W 4/028 |
| 2017/0119552 A1* | 5/2017 | Clausen | .................... | A61F 2/76 |

OTHER PUBLICATIONS

Farry, K.A.; Walker, I.D. and Baraniuk, R.G., "Myoelectric Teleoperation of a Complex Robotic Hand", Oct. 1996, IEEE Transactions on Robotics and Automation, vol. 12, No. 5.*

Harada, A.; Nakakuki, T.; Hikita, M. and Ishii, C., "Robot Finger Design for Myoelectric Prosthetic Hand and Recognition of Finger Motions via Surface EMG", Aug. 16-20, 2010, Proceedings of the 2010 IEEE International Conference on Automation and Logistics.*

Ishii, C.; Harada, A.; Nakakuki, T. And Hashimoto, H., "Control of Myoelectric Prosthetic Hand Based on Surface EMG", Aug. 7-10, Proceedings of the 2011 IEEE International Conference on Mechatronics and Automation.*

Karlsson, S., "Communication Interfaces and Protocols for Advanced Control of High-End Prosthetic Hands, Master of Science Thesis in Embedded Electronic System Design" Jun. 2015, Chalmers University of Technology.*

Al-Timemy, A.H.; Bugmann, G.; Escudero, J. and Outram, N., "Classification of Finger Movements for the Dexterous Hand Prosthesis Control with Surface Electromyography", May 2013, IEEE Journal of Biomedical and Health Informatics, vol. 17, No. 3.*

Cipriani, C.; Controzzi, M. and Carrozza, M.C., "The SmartHand Transradial Prosthesis", 2011, Journal of Neuroengineering and Rehabilitation.*

Cipriani, C.; Zaccone, F.; Micera, S. and Carrozza, M.C., "On the Shared Control of an EMG-Controlled Prosthetic Hand: Analysis of User-Prosthesis Interaction", Feb. 2008, IEEE Transactions on Robotics, vol. 24, No. 1.*

Kumar, P.; Sebastian, A.; Potluri, C.; Urfer, A.; Naidu, S. and Schoen, M., "Towards Smart Prosthetic Hand: Adaptive Probability Based Skeletan Muscle Fatigue Model", Aug. 31-Sep. 4, 2010, 32nd Annual Interational Conference of the IEEE EMBS.*

Lavars, N., "Smarty Ring Offers Connectivity Without Lifting a Finger", Dec. 10, 2013, New Atlas.*

Parrack, D., "The Ring Clock: A Wristwatch for Your Finger", Sep. 3, 2013, New Atlas.*

Quick, D., "Ring Puts the Finger on Gesture Control", Mar. 4, 2014, New Atlas.*

Ridden, P., "Genius Wireless Ring Mouse Released", May 16, 2011, New Atlas.*

Shanklin, W., "NFC Ring Lets You Unlock Your Door by Giving it the Finger", Jul. 22, 2013, New Atlas.*

Long, S., "Ring Gesture Control Device for Smart Devices", Jan. 5, 2015, TechCruch, CES 2015.*

Micera, S.; Carpaneto, J. and Raspopovic, S., "Control of Hand Prostheses Using Peripheral Information", 2010, IEEE Reviews in Biomedical Engineering, vol. 3.*

(56) References Cited

OTHER PUBLICATIONS

Naidu, D.S.; Chen, C.-H., Perez, A. and Schoen, M.P., "Control Strategies for Smart Prosthetic Hand Technology: An Overview", Aug. 20-24, 2008, 30th Annual International IEEE EMBS Conference.*

Patently Mobile, "Samsung Reveals New Circular Interface Smartwatch with Rotating Ring Controller, 3 Gesture Levels, New Charger and More", Jun. 1, 2014.*

Appendix P.: List of IBM Patents or Patent Application's Treated as Related.

Quick, Darren, "Ring puts the finger on gesture control", Mar. 4, 2014, pp. 1-7, Wearable Electronics, <http://www.gizmag.com/logbar-smart-ring-bluetooth/31080/>.

Szondy, David, "Touch Bionics introduces app-controlled prosthetic hand", pp. 1-6, Apr. 19, 2013, <http://www.gizmag.com/i-limb-ultra-revolution/27150/>.

"Samsung Reveals New Circular Interface Smartwatch with Rotating Ring Controller, 3 Gesture Levels, New Charger and More", Patent Mobility, Jun. 1, 2014, 17 pages, <http://www.patentlymobile.com/2014/06/samsung-reveals-new-circular-interface-smartwatch-with-rotating-ring-controller-3-gesture-levels-new-charger-more.html>.

Al-Timemy et al., "Classification of Finger Movements for the Dexterous Hand Prosthesis Control with Surface Electromyography", May 2013, IEEE Journal of Biomedical and Health Informatics, vol. 17, No. 3, 11 pages.

Chen et al., "Hybrid Control Strategy for Five-Fingered Smart Prosthetic Hand", Dec. 16-18, 2009, Joint 48th IEEE Converence on Decision and Control and 28th Chinese Control Conference, 6 pages.

Cipriani et al.., "On the Shared Control of an EMG-Controlled Prosthetic Hand: Analysis of User-Prosthesis Interaction", Feb. 2008, IEEE Transactions on Robotics, vol. 24, No. 1, 15 pages.

Cipriani et all.., "The SmartHand Transradial Prosthesis", 2011, Journal of Neuroengineering and Rehabilitation, 8:29, 14 pages.

Farry et al., "Myoelectric Teleoperation of a Complex Robotic Hand", Oct. 1996, IEEE Transactions on Robotics and Automation, vol. 12, No. 5., 14 pages.

Harada, A.; Nakakuki, T.; Hikita, M. and Ishii, C., "Robot Finger Design for Myoelectric Prosthetic Hand and Recognition of Finger Motions via Surface EMG", Aug. 16-20, 2010, Proceedings of the 2010 IEEE International Conference on Automation and Logistics, 6 pages.

Ishii et al., "Control of Myoelectric Prosthetic Hand Based on Surface EMG", Aug. 7-10, Proceedings of the 2011 IEEE International Conference on Mechatronics and Automation, 6 pages.

Karlsson, S., "Communication Interfaces and Protocols for Advanced Control of High-End Prosthetic Hands, Master of Science Thesis in Embedded Electronic System Design", Chalmers University of Technology, Jun. 2015, 41 pages.

Kumar et al., "Towards Smart Prosthetic Hand: Adaptive Probability Based Skeletan Muscle Fatigue Model", Aug. 31-Sep. 4, 2010, 32nd Annual International Conference of the IEEE EMBS, 4 pages.

Lavars, N., "Smarty Ring Offers Connectivity Without Lifting a Finger", New Atlas, Dec. 10, 2013, 28 pages, <http://newatlas.com/smarty-ring/30084/>.

Long, S., "Ring Gesture Control Device for Smart Devices",TechCrunch, Jan. 5, 2015, CES 2015, 5 pages, <http://techcrunch.com/video/ring-gesture-control-device-for-smart-devices/518583367/>.

Micera et al., "Control of Hand Prostheses Using Peripheral Information", 2010, IEEE Reviews in Biomedical Engineering, vol. 3, 21 pages.

Naidu et al., "Control Strategies for Smart Prosthetic Hand Technology: An Overview", Aug. 20-24, 2008, 30th Annual International IEEE EMBS Conference, 4 pages.

Parrack, D., "The Ring Clock: A Wristwatch for Your Finger", New Atlas, Sep. 3, 2013, 27 pages, <http://newatlas.com/ring-clock-wristwatch/28918/>.

Quick, D., "Ring Puts the Finger on Gesture Control", New Atlas, Mar. 4, 2014, 28 pages, <http://newatlas.com/logbar-smart-ring-bluetooth/31080/>.

Ridden, P., "Genius Wireless Ring Mouse Released", New Atlas, May 16, 2011, 39 pages, <http://newatlas.com/genius-wireless-ring-mouse-release/18639/>.

Shanklin, W., "NFC Ring Lets You Unlock Your Door by Giving it the Finger", New Atlas, Jul. 22, 2013, 29 pages, <http://newatlas.com/nfc-ring/28412/.

* cited by examiner

METHOD OF CONTROLLING PROSTHETIC DEVICES WITH SMART WEARABLE TECHNOLOGY

BACKGROUND OF THE INVENTION

The present invention relates generally to the field of prosthetics, and more particularly to controlling a prosthetic device with a wearable device.

A prosthetic device is a device that provides an artificial replacement for a missing part of the body. Common prosthetic devices include devices that replace lost arms, hands or legs. A prosthetic device may sometimes include devices such as hearing aids, which improve the existing function of a part of the body. Recent prosthetic devices incorporate a greater number of, as well as more complicated, electronic components to operate the device. Wearable technology includes non-intrusive devices a user can wear on their body without impeding daily activities. Common wearable devices include rings, watches, or bracelets.

SUMMARY

Embodiments of the present invention provide a method, system, and program product to provide mode selection of a prosthesis. A processor of a wearable device receives a first input from a user. A processor of a wearable device determines the first input indicates a change to a mode of operation of the prosthesis. A processor of a wearable device sends a first command to the prosthesis to change the mode of operation of the prosthesis.

DETAILED DESCRIPTION

Figure 1:
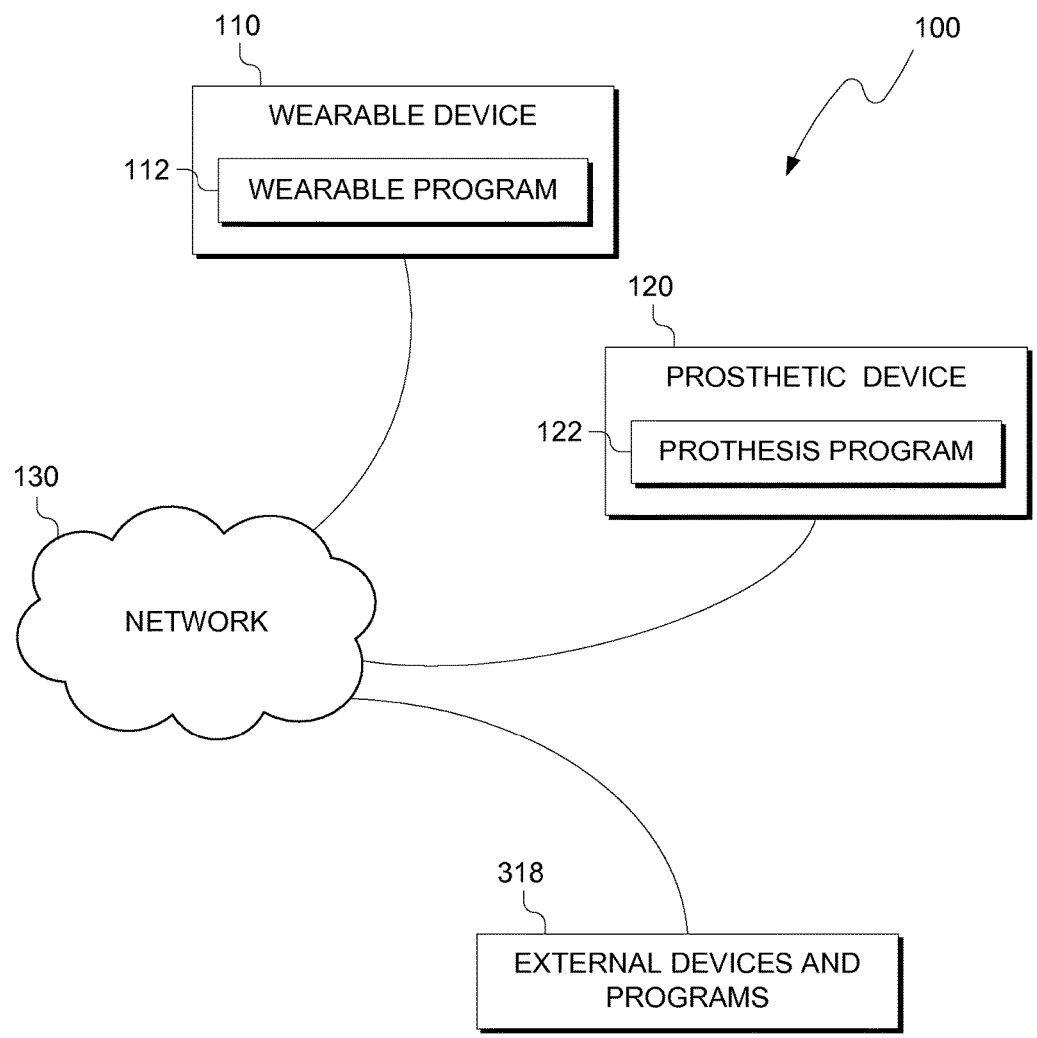
FIG. 1 is a functional block diagram illustrating a prosthesis control environment, in accordance with an exemplary embodiment of the present invention.

While solutions to prosthetic device control are known, they are cumbersome and require direct interaction with the prosthetic device to engage different modes of operation. As prosthetic devices incorporate more complex control mechanisms and operations, various different modes of operation are provided. For example, a prosthetic hand has one mode of operation where activation of the prosthetic hand closes and then extends the fingers of the hand, and another mode of operation pinch the thumb and pointer finger together when activated. Previous solutions require a direct interaction with the prosthetic hand, such as interacting with a selector switch, to change between the different modes of operation. Embodiments of the present invention recognize that by providing a non-intrusive wearable device, a user of a prosthetic device can quickly and conveniently switch between various modes of operation.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The present invention will now be described in detail with reference to the Figures. FIG. 1 is a functional block diagram illustrating prosthesis control environment, generally designated 100, in accordance with one embodiment of the present invention. Prosthesis control environment 100 includes wearable device 110 and prosthetic device 120 connected over network 130. Wearable device includes wearable program 122. Prosthetic device 120 includes prosthesis program 122. In some embodiments, prosthesis control environment 100 includes one or more external devices and programs 318, as discussed herein with respects to FIG. 3.

In various embodiments of the present invention, wearable device 110 and prosthetic device 120 each are a computing device that can be a standalone device, a server, a laptop computer, a tablet computer, a netbook computer, a personal computer (PC), or a desktop computer. In another embodiment, wearable device 110 and prosthetic device 120 each represent a computing system utilizing clustered computers and components to act as a single pool of seamless resources. In general, wearable device 110 and prosthetic device 120 can each be any computing device or a combination of devices with access to, and capable of executing wearable program 112 and prosthesis program 122. Wearable device 110 and prosthetic device 120 may include internal and external hardware components, as depicted and described in further detail with respect to FIG. 3.

In this exemplary embodiment, wearable program 112 is stored on wearable device 110. Prosthesis program 122 is stored on prosthesis device 120. However, in other embodiments, wearable program 112 and prosthesis program 122 may be stored externally and accessed through a communication network, such as network 130. Network 130 can be, for example, a local area network (LAN), a wide area network (WAN) such as the Internet, or a combination of the two, and may include wired, wireless, fiber optic or any other connection known in the art. In general, network 130 can be any combination of connections and protocols that will support communications between wearable device 110, prosthetic device 120, and external devices and program 318 in accordance with a desired embodiment of the present invention.

In various embodiments, prosthetic device 120 is a prosthesis for replacing a missing body part or enhancing an existing body part of a wearer of prosthetic device 120. For example, prosthetic device 120 may be a replacement or enhancement for an upper-extremity (e.g., arms, hands, or fingers) body part, a lower-extremity (e.g., leg, foot, or toe) body part or portion of a body part (e.g., a partial finger prosthetic). Prosthetic device 120 may also be implanted in the body of a user. For example, prosthetic device 120 administers medicine directly to the cardiovascular system of the user. In various embodiments, prosthetic device 120 includes one or more control devices to produce output for prosthetic device 120, such as movement, contraction, or expansion of prosthetic device 120 of a component of prosthetic device 120.

In an embodiment, prosthetic device 120 includes one or more activation inputs to activate the operation of prosthetic device 120. Activation inputs may include, but are not limited to, one or more sensors (e.g., one or more electromyographic (EMG) or mechanoreceptor sensors) or other electrical component (e.g., switches, buttons or the like) to detect an input from a user to activate the operation of prosthetics device 120. For example, prosthetic device 120 includes an electromyographic (EMG) sensor to detect contraction of muscles in the body of the user. When a user contracts said muscles, prosthetic device 120 activates based on the current mode of operation. If the selected mode of operation is to form a first for a prosthetic hand, then when the user contacts the muscles observed by the EMG sensor, prosthetic device 120 opens or closes the all fingers of the prosthetic hand. In one embodiment, prosthetic device 120 activates based on input received from wearable device 110, as discussed herein. In another embodiment, prosthetic device 120 activates based on sensor data generated by sensors included in prosthetics device 120 based on input from wearable device 110. In embodiments when a user provides an activation input to wearable device 110, wearable device 110 sends a respective activation command to prosthetic device 120 to activate and cause prosthetics device 120 to perform the operation of the currently selected mode.

In some embodiments, prosthetic device 120 may also include one or more sensors to collect data about the current state of prosthetic device 120. For example, a sensor for a prosthetic hand indicates which finger is extended and the degree of extension. Other sensors of prosthetic device 120 include environmental sensors. For example, a sensor provides the amount of force being applied by a surface of prosthetics device 120. Another type of sensor includes biometric sensors that provide information describing the wearer (e.g., identifying data such as a fingerprint or a vascular pattern) or a condition of the wearer (e.g., a heart rate or internal temperature of the wearer).

In various embodiments, prosthetic device 120 has one or more modes of operation. In some scenarios, different modes of operations may include different functions prosthetic device 120 is able to perform. For example, a prosthetic hand may have one mode of operation that, when activated, forms a fist. Another mode may only extend the pointer finger of the prosthetic hand, allowing a pointing gesture to be made by a wearer of the prosthetic hand. In other scenarios, different modes of operations may perform a similar operation with variations on the characteristics of the operation. For example, two operations both pinch the thumb and pointer finger of a prosthetic hand. In one mode of operation, the thumb and index finger of the prosthetic hand apply a greater amount of force. In the other mode of operation, the thumb and index finger of the prosthetic hand apply a smaller amount of force. Characteristics that can vary between modes of operations include, but not limited to, force, speed, or duration of an operation or any other variability the control devices of prosthetic device 120 can provide. One of ordinary skill in the art will appreciate that any type of mode of operation can be provided by prosthetics device 120 without deviating from the invention. A mode of operation may be a binary change in state, such as opening or closing fingers in a prosthetic hand, upon activation. Another mode of operation may vary along a range of movement, such as extending a finger of the prosthetic hand a certain amount based on receipt of each activation command. Another mode of operation may activate a series of pre-programmed movements such as, upon activation, a prosthetic hand and arm extends an arm portion of the prosthetic and grasps with the hand portion of the prosthetic.

In various embodiments, prosthetic device 120 includes prosthetic program 122. Prosthetic program 122 collects inputs from the sensors of prosthetic device 120 to determine the current state and other environmental, biometric or conditional factors. Prosthetic program 122 also provides outputs to send to the control devices of prosthetic device 120 to activate the operation currently selected. Prosthetic program 122 communicates with wearable program 112 to select a mode of operation and, in some embodiments, the activation of prosthetic device 112. Prosthetic device 120 and wearable device 110 each include a communication device to send and receive information. Each communication device is configured for communicating via wireless Personal Area Networks (WPANs) (such as via the IEEE 802.15 or 802.11 standards), infrared (IrDA), ultra wideband (UWB), and the like. While not shown, such a communications device may comprise a processor, transceiver, transmitter, receiver, or the like and an antenna embedded within prosthetic device 120 and wearable device 110, in communication therewith. As discussed herein, prosthetic device 120 and wearable device 110 may further include processing hardware and software for processing data (e.g., input data, sensor data, etc.) such as a processor or circuitry with the processing capabilities necessary for implementation of embodiments of the present invention.

In various embodiments, wearable device 110 is a device worn by a user to interact with prosthetic device 120. Wearable device 110 includes, but is not limited to, a ring, a bracelet, a watch, a pendant, or a necklace. Wearable device 110 includes one or more sensors to receive input from a user of wearable device 110. A user interacts with the sensors of wearable device 110 to select a mode of operation for prosthetic device 120. Wearable program 112 receives the input from the sensors and determines a command associated with the received input. Wearable program 112 sends the command to prosthetic program 122. In response to the received command, prosthetic program 122 configures the mode of operation of prosthetic device 120 or, in some embodiments, activates prosthetic device 120.

For example, wearable device 110 is a ring with a rotatable housing. As a user rotates the housing, a rotary sensor coupled to the ring sends input to wearable program 112. Wearable program 112 is configured to interpret input from the rotary sensor to represent a change in mode for prosthetic device 120 (e.g., for a given amount of rotation, the mode of operation for prosthetic device 120 is to be changed). Wearable program 112 sends a command to prosthetic program 122 to change the mode of operation of for prosthetic device 120. In response to receiving from wearable program 112 the command to change modes of operation, prosthetic program 122 changes the mode of operation of for prosthetic device 120. Afterwards when activated, prosthetics device 120 performs the action associated with the current mode of operation. In some embodiments, wearable program 112 sends an activation command to prosthetics program 122. Referring back to the ring example, a portion of the ring includes a touch sensitive surface. When touched by the user, the sensor sends an input signal to wearable program 112. In response, wearable program 112 sends a command to activate prosthetics device 120 to prosthetics program 122. Prosthetic program 122 operates the control devices of prosthetics device 120 based on the currently selected mode of operation.

In various embodiments, wearable device 110 detects gestures or changes in orientation as input. Wearable device includes one or more accelerometers, gyrometers, or magnetometer sensors to detect the current orientation, and any changes in orientation, of wearable device 110. In some embodiments, wearable program 112 receives the orientation and movements of wearable device 110 from the orientation sensors. As such, wearable program 112 determines if a given orientation and movement, or gesture, is detected. For example, wearable device 110 is a ring. A user could raise their hand from a resting position and wearable program 112 would determine the gesture as an activation command or a change in mode of operation command. In other embodiments, certain modes of operations of prosthetic device 120 are provided, where the movement and orientation of the body part wearable device 110 is worn upon is mirrored by prosthetic device 120. Prosthetics device 120 is a prosthesis for an opposite body part that wearable device 110 is worn upon (e.g., a ring is worn on a finger of the user and a prosthetic hand is a replacement for the opposite hand). For example, wearable device 110 is a ring. If the user rotates their hand from a parallel orientation from the ground to an orientation perpendicular to the ground, then wearable program 112 sends a command to prosthetics program 122 to mirror the movement.

One of ordinary skill in the art will appreciate that any arrangement of input sensors may be included on wearable device 110 to receive commands from a user. Inputs sensors for the wearable device may include, but are not limited to, accelerometers, switches, proximity sensors, motion detectors, touch sensors, or the like. As one skilled in the art can see, any sensor or sensors in wearable device 110 can be used without deviating from the invention, where wearable device 110 provides quick and non-intrusive mechanisms for a user to select a mode of operation for prosthetic device 120 and, in some embodiments, activate prosthetic device 120. By offering a new method of interaction with the functionality typically associated with direct interactions with a prosthesis, various embodiments of the invention provide mechanisms to interact with a prosthesis that may have been cumbersome, or in some cases impossible, without wearable device 110.

In some embodiments, wearable device 110 includes sensors to identify and authenticate a user. For example, wearable device 110 is a ring to be worn upon a user's finger. Wearable device 110 includes a vascular scanner used to determine a vein pattern of the finger the ring is worn upon. As a user places the ring onto a finger, the vascular scanner collects information describing the vein pattern and sends a model of the vein pattern to wearable program 112. Wearable program 112 determines if the vein pattern model matches a model stored in a profile of the user on wearable device 110. Based on a match being determined, wearable program 112 identifies the user's whose profile matches the received vein pattern model and authenticates the use of wearable device 110 to the user. By identifying and authenticating a wearer of wearable device 110, embodiments of the present invention provide mechanisms to prevent accidental operation of prosthetic device 120 not intended by an owner or operator of the prosthetic device 120.

In some embodiments, both wearable program 112 and prosthetic program 122 each include a cryptographic key. When wearable program 112 attempts to connect to prosthetic program 122, both wearable program 112 and prosthetic program 122 send and receive the respective keys in an exchange (e.g., a cryptographic key exchange). The shared keys can help identify and pair wearable device 110 to the correct prosthetic device 120 without input by a user. Previous solutions in pairing devices connected on a PAN required the input of a pin to connect and pair two device. A supplier of either wearable device 110 or prosthetic device 120 could saved a key pair to the respective devices when given to a user, thereby providing a simple, but secure, connection process when used.

In some embodiments, wearable device 110 includes one or more sensors to detect if wearable device 110 is being worn by a user. For example, a heart-rate sensor may be included in wearable device 110 that provides detection if wearable device 110 is being worn by the user. After authentication, the sensor keeps track of the heart-rate of the user. If no heart-rate is found, the sensor sends an indication to wearable program 112 that no heart-rate is present. In response, wearable program 112 determines that wearable device 110 has been removed (e.g., wearable device 110 is not in use). If wearable device 110 has been removed, then wearable program 112 locks wearable device 110 and stops sending commands to prosthetic program 122. As such, if wearable device 110 is dropped or otherwise not in possession by the authenticated user, then inputs received either accidentally (e.g., as the wearable device impacts the ground when dropped) or intentionally from other unauthorized users do not change the mode of operation of prosthetic device 120 or, in some embodiments, activate prosthetic device 120.

In some embodiments, wearable program 112 and prosthetic program 122 connects to external devices and programs 318. External devices and programs 318 are other computing devices and programs that can provide additional functionality to the various embodiments of the present invention. For example, a user may connect wearable device 112 to a smartphone. The smartphone includes a program to map various inputs receivable by wearable device 110 to commands that prosthetics device 120 can perform. For example, wearable device 110 is a ring with a rotatable outer ring. One user may configure a list of modes of operations for prosthetic device 120 to cycle through, when the outer ring of wearable device 110 is rotated. Another user may configure the characteristics of a mode of operation, such as changing the speed or force prosthetic device 120 operates when activated. In some embodiments, wearable program 112 or prosthetics program 122 communicate with one or more external devices and programs 318 to send and receive commands. For example, a smartphone is connected to both wearable program 112 and prosthetics program 122. Wearable program 112 sends input commands (e.g., activation commands or changes in modes of operation commands) to the smartphone. In response, the smartphone sends the commands to prosthetics program 122, thereby causing prosthetics device 120 to perform the action or instructions represented by the command.

Figure 2:
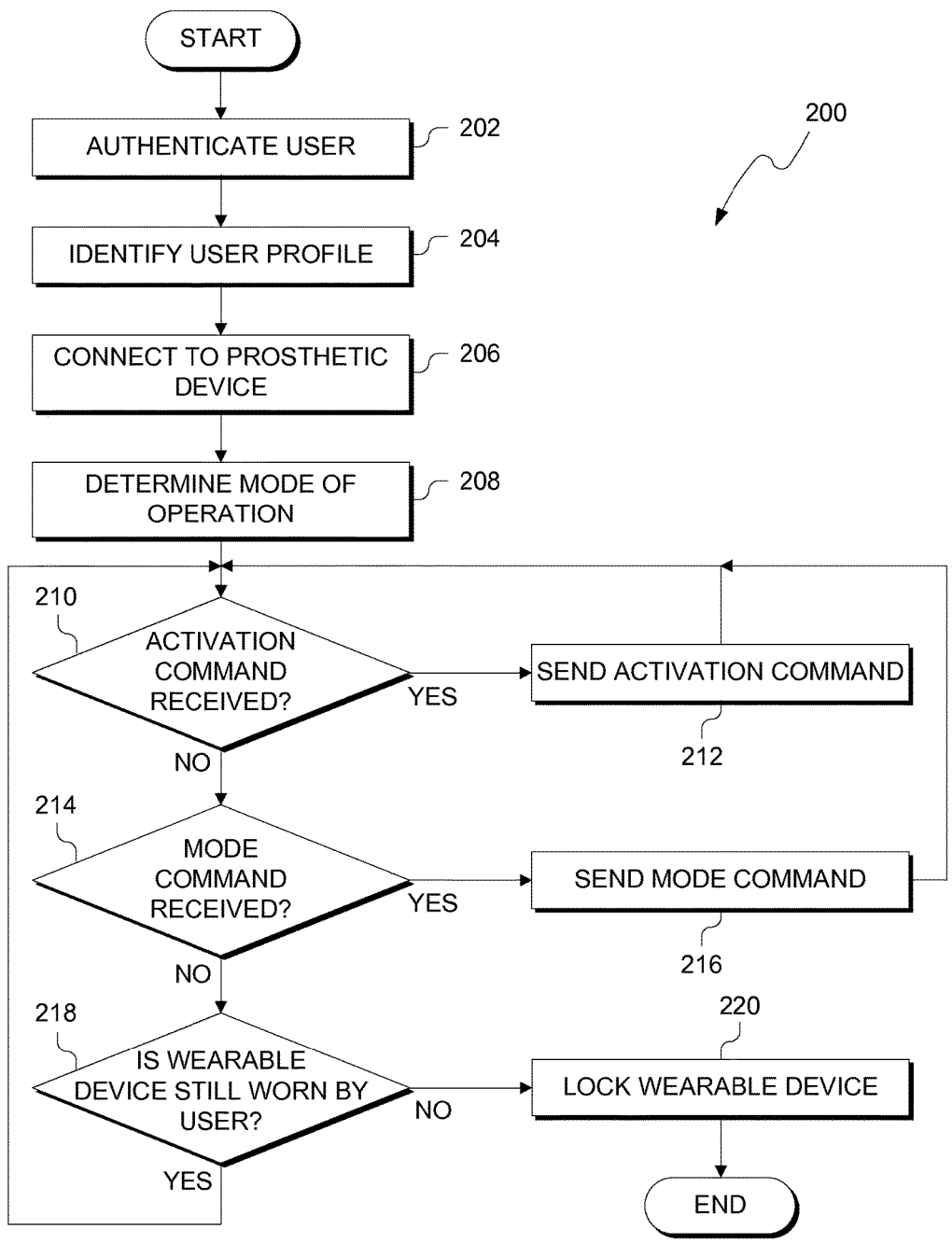
FIG. 2 illustrates operational processes of a wearable program, on a wearable device within the environment of FIG. 1, in accordance with an exemplary embodiment of the present invention.

FIG. 2 illustrates operational processes, generally designated 200, of wearable program 112, on wearable device 110 within the environment of FIG. 1, in accordance with an exemplary embodiment of the present invention.

In process 202, wearable program 112 authenticates a user wearing wearable device 110. Upon detecting that wearable device 110 is being worn be a user, wearable program 112 polls one or more authentication sensors (e.g., a vascular scanner), to determine the identity of user. Wearable program 112 compares the input received from the authentication sensors to a model describing the identity of one or more users authorized to operate wearable device 110 (e.g., the stored model of the vein pattern of an authorized user). If wearable program 112 does not find a matching profile, then wearable program 112 continues to authenticate user who wear wearable device 110 (process 202). If wearable program 112 finds a matching profile, then wearable program 112 identifies the profile of the matched user (process 204).

In process 206, wearable program 112 connects to prosthetic device 120. In some embodiments, a cryptographic key exchange is performed between wearable program 112 and prosthetics program 122 to ensure that wearable device 110 is authenticated to communicate with prosthetics device 120. When wearable device 110 connects with prosthetics device 120, wearable program 112 loads a mode of operation for prosthetic device 120 (process 208). In some cases, the profile of the user includes a default mode of operation to begin with when connected. The current mode of operation of a prosthetic device may not be clear from visual inspection. By loading a default mode of operation upon connection, the user of wearable device 110 is in knowledge of the current operation mode each time. In other cases, wearable program 112 retrieves the current mode of operation from prosthetic device 120. Upon retrieval, wearable program 112 provides an indication of the current mode of operation. For example, wearable program 112 may send a command to a smart phone to display the current mode of operation (e.g., external devices and program 318).

In process 210, wearable program 112 determines if an activation command is received by wearable device 110 from the user. If an activation command is received (YES branch of process 210), then wearable program sends the activation command to prosthetics program 112 (process 212) For example, wearable device 110 includes a touch sensitive surface. The user taps the surface to activate the prosthetic device 120. Wearable program 112 receives input from the touch surface. In response, wearable program 112 sends the activation command to prosthetics program 122 to cause prosthetics device 120 to perform the activation of the current mode of operation. In an embodiment, more than one activation command may be received by wearable device 110. Wearable program 112 receives input patterns from the input sensors of wearable device 110 (e.g., a long press versus a short press of a switch), and provides different activation commands with different characteristics, such as different levels of force for each pattern. For example, a single tap on the touch surface may cause the prosthetic device to activate at as slower speed. Whereas a double tap may cause the prosthetic device to activate at as faster speed. In some embodiments, activation of prosthetic device 120 is initiated by sensors included in prosthetic device 120 (e.g., EMG sensors detecting a muscle contraction). In such embodiments, processes 210 and subsequently 212 are not performed and only mode selection is provided by wearable device 110. In various embodiments, if wearable program 112 does not receive an activation command (NO branch of process 210), then wearable program 112 proceeds to process 214.

In process 214, wearable program 112 determines if a mode command has been received by one or more input sensors of wearable device 110. If wearable program receives a mode command (YES branch of process 216), then wearable program 112 sends the mode command to prosthetics program 122. In some embodiments, a mode command may cycle through a list of modes of operations for prosthetic device 120. For example, a rotatable ring is included in wearable device 110. For a predetermined amount of rotation, wearable program 112 sends a command to cycle through a list of modes of operations corresponding with the amount of rotation (e.g., a fifteen degree rotation cycles only one mode of operation and a thirty degree rotation cycles through two modes of operation). In other embodiments, wearable program 112 receives an input pattern from an input sensor. Based on the input pattern, wearable program 112 sends a command to change to a corresponding mode of operation for prosthetic device 120. For example, wearable device 110 includes a button. If the user taps the button three times, then wearable device 110 sends a command to change the mode of operation. As such, a user can directly change modes of operation for the prosthetic device without cycling through a list of the modes of operation. In various embodiments, if wearable program 112 does not receive a mode command (NO branch of process 214), then wearable program 112 proceeds to process 218.

In process 218, wearable program 112 determines if wearable device 110 is being worn by the user. Wearable device 110 includes one or more sensors to determine if wearable device 110 has been removed from the user. For example, a pressure sensor is included on the inside of a ring. When worn by a user, pressure is exerted onto the pressure sensor. If the pressure is removed (e.g., wearable device 110 is taken off of a finger), then wearable program 112 detects that wearable device is no longer being worn by the user. If wearable program 112 detects that wearable device 110 is still being worn by a user (YES branch of process 218), then wearable program 112 continues receiving, processing and sending both mode commands (processes 214 and 216) and, in some embodiments, activation commands (processes 210 and 212). If wearable program 112 determines that wearable device is no longer being worn by the user (NO branch of process 218), the wearable program 112 locks wearable device 110 (process 220). As such, wearable program 112 prevents commands to be sent to prosthetics device 120 until wearable device is worn by the user and the user is authenticated again, as discussed in process 202.

Figure 3:
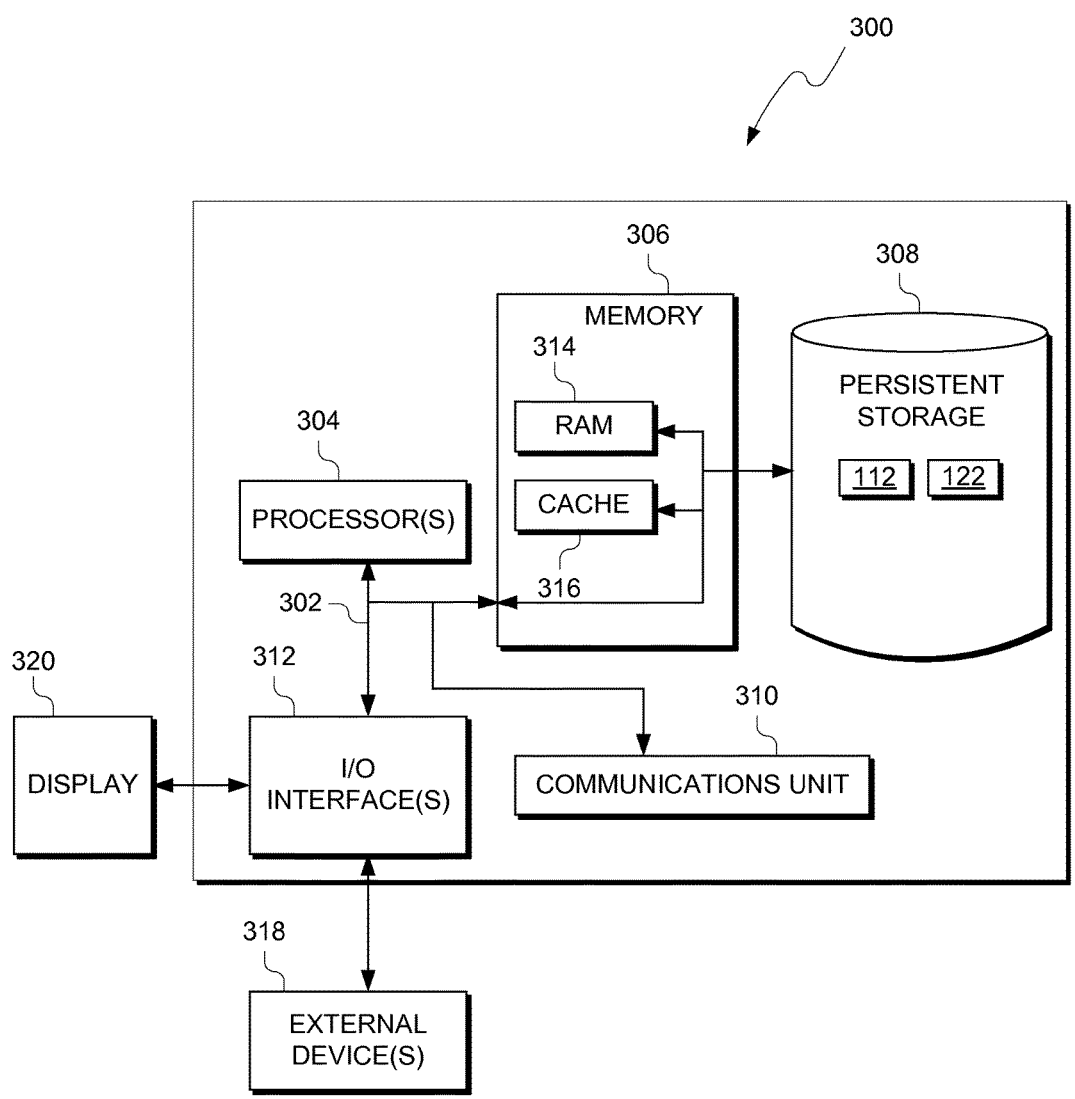
FIG. 3 depicts a block diagram of components of the computing device executing a wearable program and a prosthesis program, in accordance with an exemplary embodiment of the present invention.

FIG. 3 depicts a block diagram, 300, of components for each of wearable device 110 and prosthetic device 120, in accordance with an illustrative embodiment of the present invention. It should be appreciated that FIG. 3 provides only an illustration of one implementation and does not imply any limitations with regard to the environments in which different embodiments may be implemented. Many modifications to the depicted environment may be made.

Wearable device 110 and prosthetic device 120 each include communications fabric 302, which provides communications between computer processor(s) 304, memory 306, persistent storage 308, communications unit 310, and input/output (I/O) interface(s) 312. Communications fabric 302 can be implemented with any architecture designed for passing data and/or control information between processors (such as microprocessors, communications and network processors, etc.), system memory, peripheral devices, and any other hardware components within a system. For example, communications fabric 302 can be implemented with one or more buses.

Memory 306 and persistent storage 308 are computer-readable storage media. In this embodiment, memory 306 includes random access memory (RAM) 314 and cache memory 316. In general, memory 306 can include any suitable volatile or non-volatile computer-readable storage media.

Wearable program 112 and prosthesis program 122 are stored in persistent storage 308 for execution and/or access by one or more of the respective computer processors 304 via one or more memories of memory 306. In this embodiment, persistent storage 308 includes a magnetic hard disk drive. Alternatively, or in addition to a magnetic hard disk drive, persistent storage 308 can include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 308 may also be removable. For example, a removable hard drive may be used for persistent storage 308. Other examples include optical and magnetic disks, thumb drives, and smart cards that are inserted into a drive for transfer onto another computer-readable storage medium that is also part of persistent storage 308.

Communications unit 310, in these examples, provides for communications with other data processing systems or devices, including resources of network 130. In these examples, communications unit 310 includes one or more network interface cards. Communications unit 310 may provide communications through the use of either or both physical and wireless communications links. Wearable program 112 and prosthesis program 122 may be downloaded to persistent storage 308 through communications unit 310.

I/O interface(s) 312 allows for input and output of data with other devices that may be connected to wearable device 110 or prosthetic device 120. For example, I/O interface 312 may provide a connection to external devices 318 such as a keyboard, keypad, a touch screen, and/or some other suitable input device. External devices 318 can also include portable computer-readable storage media such as, for example, thumb drives, portable optical or magnetic disks, and memory cards. Software and data used to practice embodiments of the present invention, e.g., wearable program 112 and prosthesis program 122, can be stored on such portable computer-readable storage media and can be loaded onto persistent storage 308 via I/O interface(s) 312. I/O interface(s) 312 also connect to a display 320.

Display 320 provides a mechanism to display data to a user and may be, for example, a computer monitor, or a television screen.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

It is to be noted that the term(s) "Smalltalk" and the like may be subject to trademark rights in various jurisdictions throughout the world and are used here only in reference to the products or services properly denominated by the marks to the extent that such trademark rights may exist.

What is claimed is:

1. A method for mode selection of a prosthesis, the method comprising:
   receiving, by a wearable device, a first input from a user, wherein (i) the wearable device is a ring that comprises a rotatable housing with a touch surface sensitive surface, and (ii) the first user input comprises the user touching the touch surface;
   determining, by the wearable device, the first input indicates a change to a user-activated mode of operation of the prosthesis;
   sending, by the wearable device, a first command to the prosthesis to change the user-activated mode of operation of the prosthesis;
   in response to receiving the first command by the prosthesis, operating one or more control devices of the prosthesis to change a current user-activated mode of operation of the prosthesis based, at least in part, on the determined user-activated mode of operation associated with the received first input;
   receiving, by the wearable device, a second input from a user;
   determining, by the wearable device, the second input indicates an activation operation of the prosthesis;
   sending, by the wearable device, a second command to the prosthesis to activate the prosthesis; and
   in response to receiving the second command by the prosthesis, operating the one or more control devices of the prosthesis to perform an action associated with the current user-activated mode of operation of the prosthesis.

2. The method of claim 1, the method further comprising:
   in response to the user rotating the rotatable housing, sending, by the wearable device, the first command.

3. The method of claim 1, the method further comprising:
   in response to the user contacting the touch sensitive surface, sending, by the wearable device, the second command.

4. The method of claim 1, the method further comprising:
   determining, by the wearable device, an identity of the user;
   identifying, by the wearable device, a profile of the user based, at least in part, of the identity of the user; and
   connecting, by the wearable device, to a prosthetic device associated with the profile of the user.

5. The method of claim 1, the method further comprising:
   in response to a detection that the wearable device is removed, preventing, by the wearable device, the sending of the first command.

\* \* \* \* \*